United States Patent
Oraby (10) Patent No.: US 9,696,250 B2
(45) Date of Patent: Jul. 4, 2017

(54) RELAXIVITY-INSENSITIVE MEASUREMENT OF FORMATION PERMEABILITY

(75) Inventor: Moustafa E. Oraby, Cairo (EG)

(73) Assignee: Halliburton Energy Services, Inc., Houston, TX (US)

( * ) Notice: Subject to any disclaimer, the term of this patent is extended or adjusted under 35 U.S.C. 154(b) by 938 days.

(21) Appl. No.: 14/111,143

(22) PCT Filed: Apr. 18, 2011

(86) PCT No.: PCT/US2011/032863
§ 371 (c)(1),
(2), (4) Date: Oct. 10, 2013

(87) PCT Pub. No.: WO2012/144976
PCT Pub. Date: Oct. 26, 2012

(65) Prior Publication Data
US 2014/0033815 A1 Feb. 6, 2014

(51) Int. Cl.
*G01V 3/00* (2006.01)
*G01N 15/08* (2006.01)
*G01V 3/32* (2006.01)

(52) U.S. Cl.
CPC ............... *G01N 15/08* (2013.01); *G01V 3/32* (2013.01)

(58) Field of Classification Search
CPC ....................................................... G01V 3/32
(Continued)

(56) References Cited

U.S. PATENT DOCUMENTS 5,069,065 A 12/1991 Sprunt et al.
5,663,073 A 9/1997 Oraby
(Continued)

FOREIGN PATENT DOCUMENTS

WO WO-2012/144976 A1 10/2012

OTHER PUBLICATIONS

PCT International Search Report and Written Opinion, dated Jul. 5, 2011, Appl No. PCT/US2011/032863, "Relaxivity-Insensitive Measurement of Formation Permeability" filed Apr. 18, 2011, 11 pgs.
(Continued)

*Primary Examiner* — Louis Arana
(74) *Attorney, Agent, or Firm* — Iselin Law PLLC; Alan Bryson (57) ABSTRACT

Systems and methods that provide relaxivity-insensitive permeability logs. At least some logging system embodiments include a logging tool assembly that measures spin-spin relaxation time distributions of formation fluid nuclei at different positions along a borehole. A processor operates on the measurements to provide a permeability log that is relatively insensitive to relaxivity coefficient changes and hence insensitive to changes in formation fluids. Thus, permeability logs will be relatively unaffected by invasion of the borehole fluids into the formation, even if surfactants in the borehole fluid cause large changes in formation wettability. For each position logged within a borehole, the processor may process the measured relaxation time distribution to determine a Swanson parameter value; adjust the Swanson parameter value to reduce dependence on relaxivity; and convert the adjusted value to a permeability measurement. Examples are included below to demonstrate the markedly increased permeability measurement accuracy.

19 Claims, 9 Drawing Sheets

(58) Field of Classification Search
USPC .................................... 324/303, 306, 309
See application file for complete search history.

(56) References Cited

U.S. PATENT DOCUMENTS

| | | |
|---|---|---|
| 5,668,369 A | 9/1997 | Oraby |
| 6,072,314 A | 6/2000 | Oraby |
| 6,559,639 B2 | 5/2003 | Minh et al. |
| 6,833,698 B2 | 12/2004 | Sun et al. |
| 7,255,166 B1 | 8/2007 | Weiss |
| 7,257,490 B2 | 8/2007 | Georgi et al. |
| 7,356,413 B2 | 4/2008 | Georgi et al. |
| 7,363,161 B2 | 4/2008 | Georgi et al. |
| 7,716,028 B2 | 5/2010 | Montaron et al. |
| 8,387,743 B2 | 3/2013 | Oraby |
| 8,440,960 B2 | 5/2013 | Oraby et al. |
| 8,510,051 B2 | 8/2013 | Oraby |
| 2008/0082270 A1 | 4/2008 | Heaton et al. |
| 2010/0277167 A1 | 11/2010 | Romero |
| 2013/0057277 A1* | 3/2013 | Zielinski ............ G01V 3/32 324/303 |
| 2016/0139291 A1* | 5/2016 | Saidian ............ G01V 3/32 324/303 |

OTHER PUBLICATIONS

Mandour, et al., "Linear vs. Nonlinear Porosity Estimation of NMR Oil Reservoir Data", IIUM Engineering Journal, vol. 8, No. 1, 2007, pp. 19-33, [retrieved on Jun. 20, 2011], retrieved from the Internet <URL: http://www.iium.edu.my/ejournal/home2010/index.php/iiumej/article/download/85/47>.

PCT International Preliminary Report on Patentability, dated Jun. 6, 2013, Appl No. PCT/US2011/032863, "Relaxivity-Insensitive Measurement of Formation Permeability" filed Apr. 18, 2011, 4 pgs.

* cited by examiner

Permeability Comparison - Water Wet Rock

| Sample # | Core Perm | Swanson Perm | Oraby Perm | Coates Perm | SBVI Perm |
|---|---|---|---|---|---|
| 1 | 1044 | 984.8 | 1119.5 | 2310.9 | 2435.9 |
| 2 | 345 | 425.7 | 324.4 | 296.9 | 357.1 |
| 3 | 1.7 | 1.9 | 2 | 1.6 | 5.6 |
| 4 | 23 | 18.7 | 28.1 | 19.9 | 39.6 |

Permeability Comparison – Oil Wet Altered Rock (OBM Effect)
Highly Oil Wet Case : Rock Relaxivity to oil is 10x water

| Sample # | Core Perm | Swanson Perm | Oraby Perm | Coates Perm | SBVI Perm |
|---|---|---|---|---|---|
| 1 | 1044 | 1.4 | 898.3 | 232 | 159.4 |
| 2 | 345 | 0.6 | 328.2 | 51.8 | 49.4 |
| 3 | 1.7 | 0 | 2.1 | 0.2 | 1.1 |
| 4 | 23 | 0 | 30.6 | 2.2 | 7 |

Permeability Comparison - Oil Wet Altered Rock (OBM Effect)
Medium Oil Wet Case : Rock Relaxivity to oil is 3x water

| Sample # | Core Perm | Swanson Perm | Oraby Perm | Coates Perm | SBVI Perm |
|---|---|---|---|---|---|
| 1 | 1044 | 46.7 | 983.3 | 812.4 | 640.4 |
| 2 | 345 | 20 | 345.6 | 143.9 | 145.3 |
| 3 | 1.7 | 0.1 | 1.9 | 0.7 | 2.3 |
| 4 | 23 | 0.8 | 27.1 | 9.8 | 16.7 |

RELAXIVITY-INSENSITIVE MEASUREMENT OF FORMATION PERMEABILITY

BACKGROUND

Oil field operators demand access to a great quantity of information regarding the parameters and conditions encountered downhole. Such information typically includes characteristics of the earth formations traversed by the borehole and data relating to the size and configuration of the borehole itself. The measured parameters are usually recorded and displayed in the form of a log, i.e., a two-dimensional graph showing the measured parameter as a function of tool position or depth. The collection of information relating to conditions downhole, which commonly is referred to as "logging," can be performed by several methods including wireline logging, tubing-conveyed logging, and "logging while drilling" (LWD).

In wireline logging, a sonde is lowered into the borehole after some or all of the well has been drilled. The sonde hangs at the end of a long cable or "wireline" that provides mechanical support to the sonde and also provides an electrical connection between the sonde and electrical equipment located at the surface of the well. In accordance with existing logging techniques, various parameters of the earth's formations are measured and correlated with the position of the sonde in the borehole as the sonde is pulled uphole.

Tubing-conveyed logging is similar to wireline logging, but the sonde is mounted on the end of a tubing string. The tubing string's rigidity enables the tubing-conveyed sonde to travel where it would be difficult to send a wireline sonde, e.g., along horizontal or upwardly-inclined sections of the borehole. The tubing string can include embedded conductors in the tubing wall for transporting power and telemetry, or a wireline cable can be fed through the interior of the tubing string, or the sonde can simply store data in memory for later retrieval when the sonde returns to the surface.

In LWD, the drilling assembly includes sensing instruments that measure various parameters as the formation is being drilled, thereby enabling measurements of the formation while it is less affected by fluid invasion. While LWD measurements are desirable, drilling operations create an environment that is generally hostile to electronic instrumentation, telemetry, and sensor operations.

Nuclear magnetic resonance (NMR) logging tools are available for use in each of these environments. NMR tools operate by using an imposed static magnetic field, $B_0$, to give nuclei with non-zero nuclear spin (non-zero angular momentum) split energy levels. Since lower energy levels are preferred, an ensemble of nuclei will exhibit an anisotropic distribution of energy states, giving the nuclear spins a preferential polarization parallel to the imposed field. This state creates a net magnetic moment, producing a bulk magnetization. The nuclei (primarily hydrogen nuclei) converge upon their equilibrium alignment with a characteristic exponential relaxation time constant. When this convergence occurs after the nuclei have been placed in a cooperative initial state (discussed below), it is known as recovery. The time constant for recovery is called the "spin-lattice" or "longitudinal" relaxation time $T_1$.

During or after the polarization period, the tool applies a perturbing field, usually in the form of a radio frequency electromagnetic pulse whose magnetic component, $B_1$, is perpendicular to the static field $B_0$. This perturbing field moves the orientation of the magnetization into the transverse (perpendicular) plane. The frequency of the pulse can be chosen to target specific nuclei (e.g., hydrogen). The polarized nuclei are perturbed simultaneously and, when the perturbation ends, they precess around the static magnetic field gradually re-polarizing to align with the static field once again while losing coherence in the transverse plane ($T_2$ relaxation). The precessing nuclei generate a detectable radio frequency signal that can be used to measure statistical distributions of $T_1$, $T_2$, porosities, and/or diffusion constants.

The transverse relaxation time (also called the "spin-spin" relaxation time) represents how quickly the transverse plane magnetization disperses through de-phasing and magnitude loss. Forces aligned with the transverse plane contribute to non-adiabatic, non-reversible, relaxation while those aligned with the static field contribute to adiabatic, reversible relaxation. The intrinsic transverse time relaxation constant, i.e., relaxation that is solely attributable to non-adiabatic effects, is labeled as "$T_2$" and it is solely a property of the substance. The measured transverse relaxation time constant, however, is also influenced by environmental factors and field inhomogeneities that cause the magnetization to dephase. The time constant for all transverse relaxation processes together (intrinsic and environmental) is usually labeled as "$T_2^*$".

To isolate the intrinsic $T_2$ subsequent RF pulses can be applied to invert the spin phases and cause the net magnetization to gradually refocus into phase, thus rebuilding the induced signal to create "spin echoes". After each echo signal peaks (at the time when the nuclei are back in phase), the signal begins to decay again in the same manner as before. Another fellow-up pulse can be used to again reverse the instantaneous phases and thereby rebuild the signal again to a subsequent echo.

By using a series of follow-up pulses, the signal is periodically rebuilt after each dephasing, although each rebuilding is to a slightly lesser peak amplitude due to the intrinsic losses in magnetization so eventually the echo signals die out completely. The time constant associated with the decay of the recurring spin echo amplitudes approaches the transverse relaxation time $T_2$. (Molecular motion through gradients cause another irreversible spreading of the magnetization so the true $T_2$ can only be measured in a perfectly uniform magnetic field.)

A sequence of refocusing pulses is known in the art as the Carr-Purcell-Meiboom-Gill (CPMG) pulse sequence. It is most frequently used for measuring $T_2$ distributions. A popular method for measuring $T_1$ distribution employs observing the effect of different recovery time spacings between separate CPMG experiments. Other methods utilizing consecutively spaced RF perturbations followed by a CPMG sequence can also be employed to probe the magnetization build up. As is well known in the industry, the relaxation time distribution information from either $T_2$ or $T_1$ can be readily converted into measurements of porosity (i.e., the relative amount of void space in the formation), hydrocarbon saturation (i.e., the relative percentage of hydrocarbons and water in the formation fluid), and permeability (i.e., the ability of formation fluid to flow from the formation into the well bore). For a more comprehensive overview of the NMR technology including logging methods and various tool designs, the interested reader is directed, for example, to the book by Coates et al. entitled "NMR Logging: Principles and Applications" distributed by Gulf Publishing Company (2000), and hereby incorporated herein by reference for background.

At least some of the existing methods for converting NMR tool measurements into formation permeability logs rely on calibration parameters. These calibration parameters can be determined by from laboratory experiments on core samples. However, the calibration parameters are generally different depending on whether the pore spaces contain water or oil. Moreover, as borehole fluids invade the formation, the pore fluids can change in a manner that unpredictably affects the permeability log.

DESCRIPTION OF THE DRAWINGS

A better understanding of the various disclosed embodiments can be obtained when the following detailed description is considered in conjunction with the following drawings, in which.

While the invention is susceptible to various modifications and alternative forms, specific embodiments thereof are shown by way of example in the drawings and will herein be described in detail. It should be understood, however, that the drawings and detailed description thereto are not intended to limit the disclosure to the particular illustrated embodiments, but on the contrary, the intention is to cover all modifications, equivalents and alternatives falling within the scope of the appended claims.

DETAILED DESCRIPTION

The issues identified in the background are at least in part addressed by systems and methods that provide relaxivity-insensitive permeability logs. At least some logging system embodiments include a logging tool assembly that measures spin-spin relaxation time distributions of formation fluid nuclei at different positions along a borehole. A processor operates on the measurements to provide a permeability log that is relatively insensitive to relaxivity coefficient changes and hence insensitive to changes in formation fluids. Thus, permeability logs will be relatively unaffected by invasion of the borehole fluids into the formation, even if surfactants in the borehole fluid cause large changes in formation wettability. For each position logged within a borehole, the processor may process the measured relaxation time distribution to determine a Swanson parameter value; adjust the Swanson parameter value to reduce dependence on relaxivity; and convert the adjusted value to a permeability measurement. Examples are included below to demonstrate the markedly increased permeability measurement accuracy over a range of circumstances including water-wet rock, oil-wet rock, and wettability-altered (i.e., borehole-fluid invaded) rock.

Figures 1, 2:
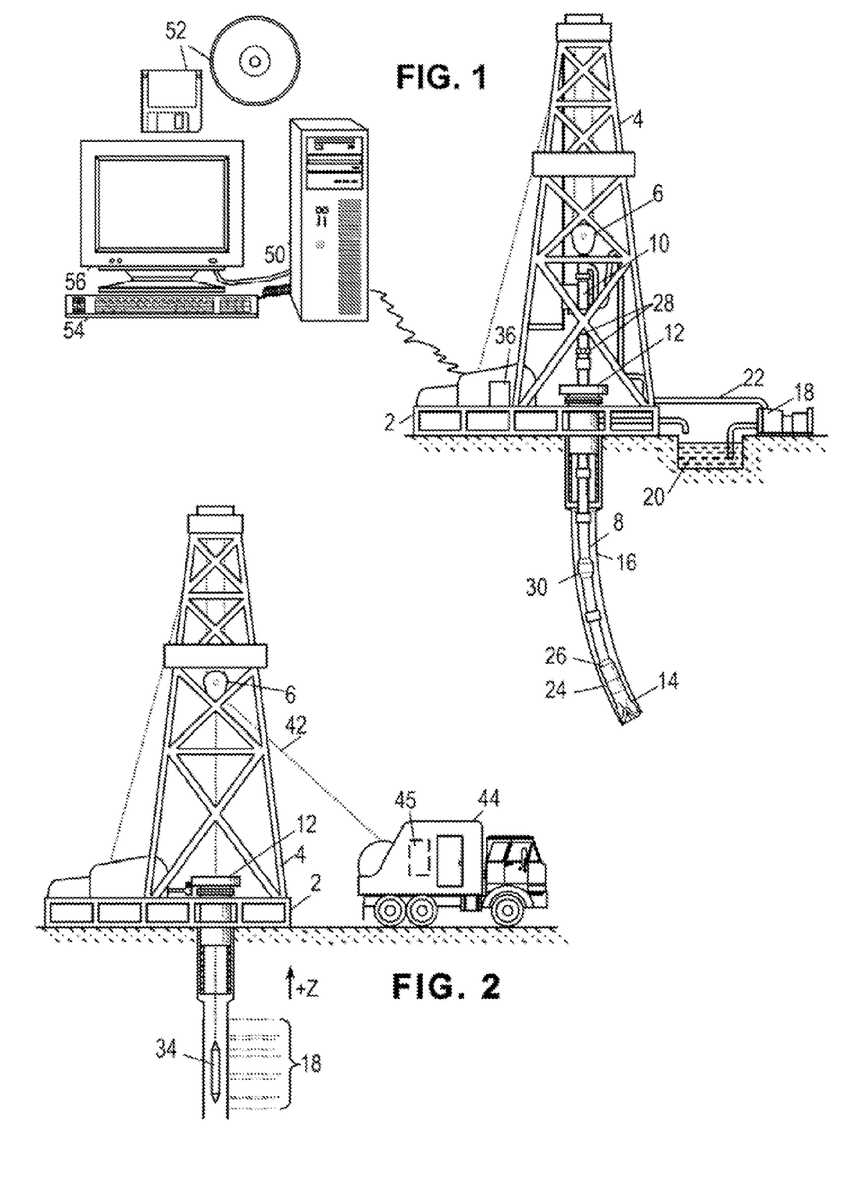
FIG. 1 shows an illustrative environment for logging while drilling ("LWD")
FIG. 2 shows an illustrative environment for wireline logging.

The disclosed systems and methods are best understood in a suitable usage context. Accordingly, FIG. 1 shows an illustrative logging while drilling (LWD) environment. A drilling platform 2 supports a derrick 4 having a traveling block 6 for raising and lowering a drill string 8. A top drive 10 supports and rotates the drill string 8 as the string is lowered through a well head 12. The drill string's rotation (and/or a downhole motor) drives a drill bit 14 to extend the borehole 16. Mud recirculation equipment 18 draws drilling fluid from a retention pit 20 and pumps it through a feed pipe 22 to top drive 10, through the interior of drill string 8 to the drill bit 14, through orifices in drill bit, through the annulus around drill string 8 to a blowout preventer at the surface, and through a discharge pipe into the pit 20. The drilling fluid transports cuttings from the borehole into the pit 20 and aids in maintaining the borehole integrity.

A nuclear magnetic resonance (NMR) LEWD tool 24 is integrated into the bottom-hole assembly near the bit 14. As the bit extends the borehole through the formations, the NMR tool collects measurements relating to spin relaxation time ($T_1$, $T_2$, and/or $T_2^*$) distributions as a function of depth or position in the borehole. Other tools and sensors can also be included in the bottomhole assembly to gather measurements of various drilling parameters such as position, orientation, weight-on-bit, borehole diameter, etc. Control/telemetry module 26 collects data from the various bottomhole assembly instruments (including position and orientation information) and stores them in internal memory. Selected portions of the data can be communicated to surface receivers 28 by, e.g., mud pulse telemetry. Other logging-while drilling telemetry methods also exist and could be employed. For example, electromagnetic telemetry or through-wall acoustic telemetry can be employed with an optional repeater 30 to extend the telemetry range. As another example, the drill string if could be formed from wired drillpipe that enables waveforms or images to be transmitted to the surface in real time to enable quality control and processing to optimize the logging resolution. Most telemetry systems also enable commands to be communicated from the surface to the control and telemetry module to configure the operation of the tools.

For mud pulse telemetry, telemetry module 26 modulates a resistance to drilling fluid flow to generate pressure pulses that propagate to the surface. One or more pressure transducers 28 convert the pressure signal into electrical signal(s) for sampling and digitization by a data acquisition system 36, which then communicates the digital data to a computer system 50 or some other form of a data processing device. Computer 50 operates in accordance with software (which may be stored on information storage media 52) and user input received via an input device 54 to process and decode the received signals. The resulting telemetry data may be further analyzed and processed by computer 50 to generate a display of useful information on a computer monitor 56 or some other form of a display device. For example, a driller could employ this system to obtain and view a relaxivity-insensitive permeability log.

At various times during the drilling process, the drill string 8 may be removed from the borehole as shown in FIG. 2. Once the drill string has been removed, logging operations can be conducted using a wireline logging tool 34, i.e., a sensing instrument sonde suspended by a cable 42 having conductors for transporting power to the tool and telemetry from the tool to the surface. The wireline logging tool 34 may have pads and/or centralizing springs to maintain the tool near the axis of the borehole as the tool is pulled uphole. As explained further below, tool 34 can include an NMR logging instrument that collects relaxation time distribution measurements. A logging facility 44 collects measurements from the logging tool 34, and includes a computer system 45 for processing and storing the measurements gathered by the logging tool. Tubing-conveyed logging is similar to wireline logging, except that a tubing string is used to move the NMR logging instrument through the borehole.

In each of the foregoing logging environments, the logging tool assemblies may include a navigational sensor package that includes direction sensors for determining the inclination angle, the horizontal angle, and the rotational angle (a.k.a. "tool face angle") of the bottom hole assembly. As is commonly defined in the art, the inclination angle is the deviation from vertically downward, the horizontal angle is the angle in a horizontal plane from true North, and the tool face angle is the orientation (rotational about the tool axis) angle from the high side of the wellbore. In accordance with known techniques, wellbore directional measurements can be made as follows: a three axis accelerometer measures the earth's gravitational field vector relative to the tool axis and a point on the circumference of the tool called the "tool face scribe line". (The tool face scribe line is typically drawn on the tool surface as a line parallel to the tool axis.) From this measurement, the inclination and tool face angle of the bottom hole assembly can be determined. Additionally, a three axis magnetometer measures the earth's magnetic field vector in a similar manner. From the combined magnetometer and accelerometer data, the horizontal angle of the bottom hole assembly may be determined. A motion sensing unit can also be included to track the position of the tool. In many cases, the motion sensing unit can derive the position information from the direction sensors.

Nuclear magnetic resonance tools cause hydrogen nuclei to oscillate in a magnetic field. As the tool manipulates the spin of these nuclei, the tool's antennas detect echo signals which can be expressed in the following form:

$$E_i = \sum_{k=1}^{k=N} \phi_k e^{-\frac{t_i}{(T_2)_k}}, \quad (1)$$

$$i = 0, 1, 2, 3, \ldots$$

where the range of possible $T_2$ relaxation time values is divided into N bins with $(T_2)_k$ being a representative spin-spin relaxation time value for the kth bin, and with $\phi_k$ being the population of nuclei in the kth bin. The population of hydrogen nuclei in a given bin, $\phi_k$ is proportional to the amount of fluid in a formation pore of a given size, and hence $\phi_k$ is also known as "incremental porosity". The incremental porosity values can be readily extracted from the detected echo signals using commercially available software such as the LogIC software available from Logicom E&P Ltd, Buckinghamshire UK. Measured $T_2$ distributions are commonly expressed as a plot of incremental porosity $\phi_k$ versus relaxation time $(T_2)_k$ (see, e.g., FIGS. 3 and 5-6).

The spin-spin relaxation time $(T_2)$ for a given population has an associated formation pore size which is usually expressed in terms of a ratio between the pore's surface area (S) and volume (V). The commonly-accepted relationship between pore size and spin-spin relaxation time $(T_2)$ is:

$$\frac{1}{T_2} = \rho \frac{S}{V} \quad (2)$$

where S/V is the surface to volume ratio of the pore, and p is an experimentally-measured surface relaxivity. The surface relaxivity varies with the fluid type (e.g., water, hydrocarbon), so fluid type should be taken into account when estimating pore size distribution and total porosity.

Figure 3:
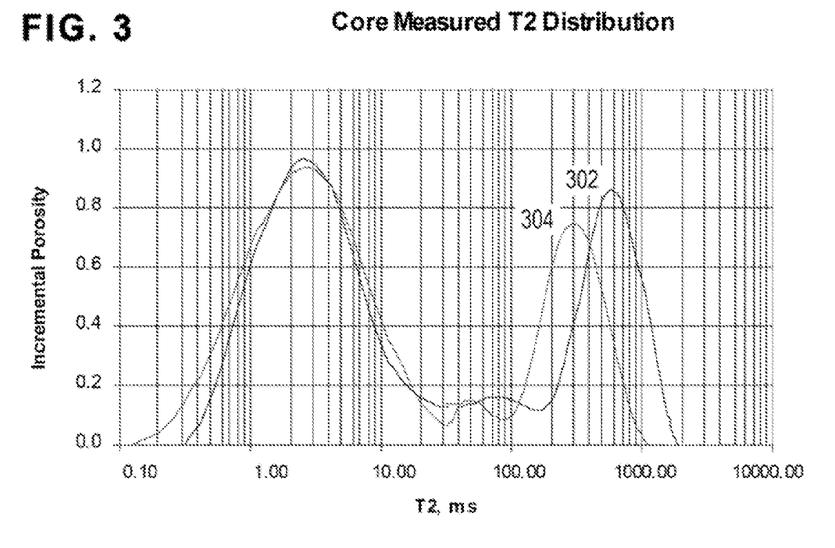
FIG. 3 shows an illustrative T2 distribution.

FIG. 3 shows illustrative $T_2$ (spin-spin) relaxation time distributions for a formation core sample. Curve 302 shows the distribution for the core sample in its original "water wet" condition, meaning that the surfaces of the formation matrix are coated with water. After being soaked for 96 hours in an oil-based mud (OBM) having surfactants, the distribution shifts as indicated by curve 304. A number of methods exist for converting a relaxation time distribution measurement into a measure of formation permeability. As we show below, each of these existing methods is overly sensitive to this relaxivity-induced distribution shift.

The three existing methods discussed here are the Coates method, the Spectral Bulk Volume Irreducible (SBVI) method, and the Swanson method. The Coates' formula for permeability K is:

$$K = \left(\frac{\phi}{C}\right)^\alpha \left(\frac{\phi_f}{\phi_b}\right)^\beta \quad (3)$$

where $\phi_f$ is free fluid porosity, $\phi_b$ is bound fluid porosity, $\phi$ is total porosity ($\phi_f + \phi_b$), and $\alpha$, $\beta$, C, and $T2_{cutoff}$ are adjustable model parameters. The porosity values are determined by summing up incremental porosities above and below the $T2_{cutoff}$, which can be roughly chosen as a minimum in the distribution curve between about 20 and 40 ms. (Areas above the T2cutoff represent free fluids, while areas below the T2cutoff represent bound fluids.) For FIG. 3, the Coates model parameters are $T2_{cutoff}$=33 ms, $\alpha$=4, $\beta$=2, and C=10. The calibrated permeability measurement for curve 302 is K=236 millidarcies (mD). For the shifted curve, the permeability measurement falls by 43% to 1.34 mD.

The SBVI method employs the Coates formula (3), but rather than using a $T2_{cutoff}$ parameter, the SBVI calculates bound porosity $\phi_b$ using the following formula:

$$\phi_b = \sum_{k=1}^{N} \frac{\phi_k}{\alpha(T_2)_k + 1} \quad (4)$$

As will be shown further below, the SBVI retains a marked sensitivity to the shift in relaxation time distribution.

The Swanson method takes the following approach. For each of the bins in the T2 distribution, the system determines a product of that bin's relaxation time $(T_2)_k$ with a sum of porosities from that bin upward. The maximum product is then identified and is herein referred to as the Swanson parameter:

$$(S_b T_2)_{max} = \max_{i \in 1 \ldots N} \left[(T_2)_i \sum_{k=i}^{k=N} \phi_k\right] \quad (5)$$

Figure 4:
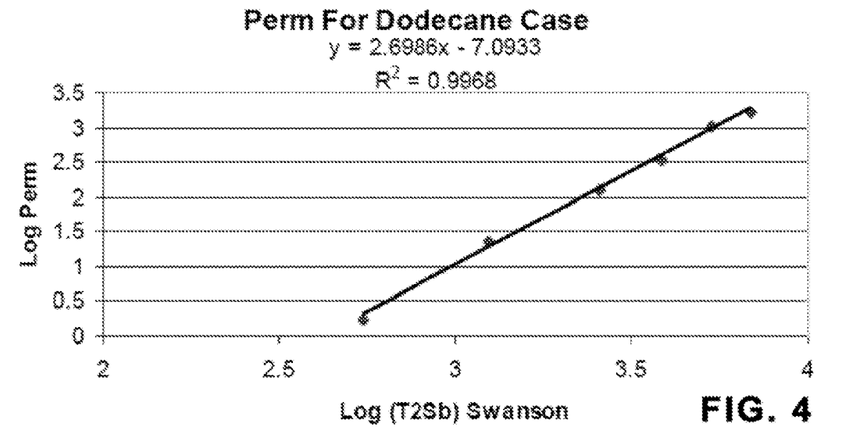
FIG. 4 shows an illustrative relationship between permeability and the Swanson parameter.
Figure 5A:
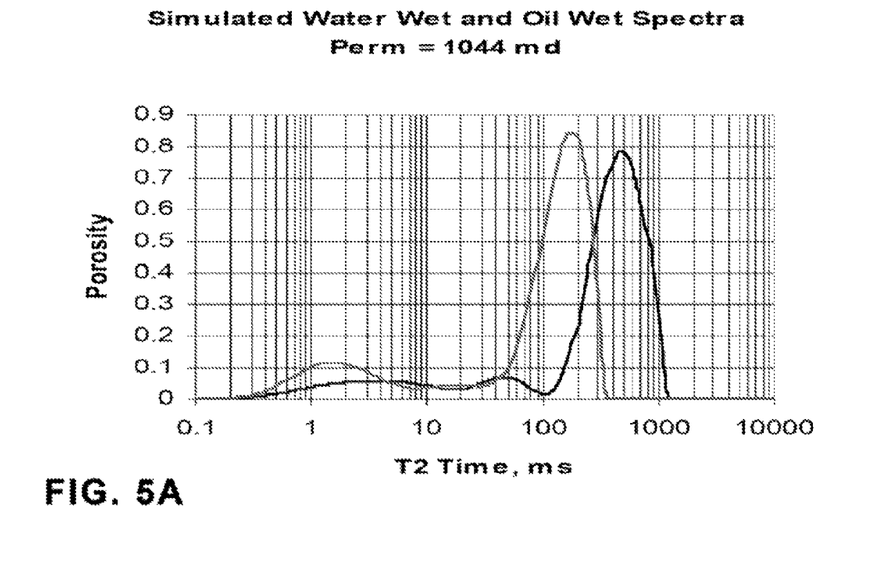
FIGS. 5a-5d show illustrative oil-wet and water-wet T2 distributions for different permeabilities for a relaxivity ratio of 10.
Figure 5B:
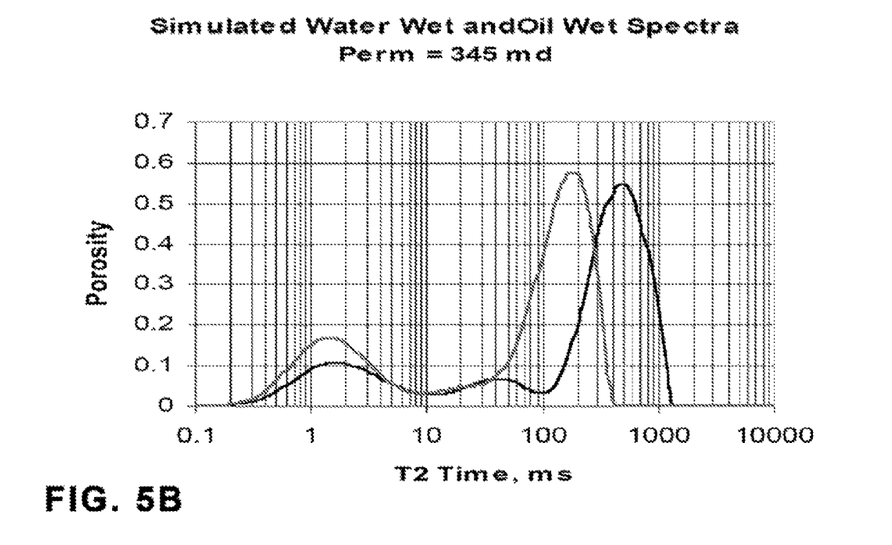
Figure 5C:
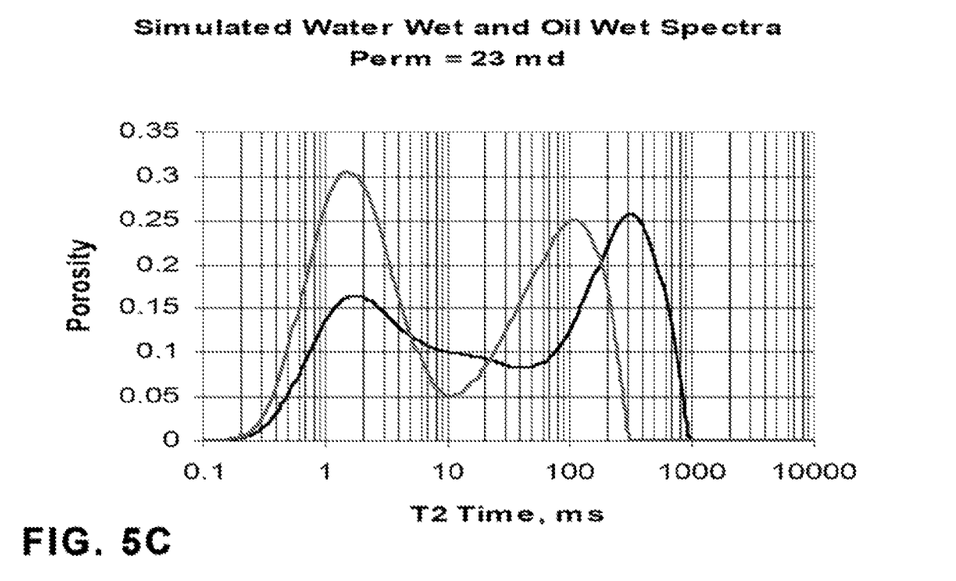
Figure 5D:
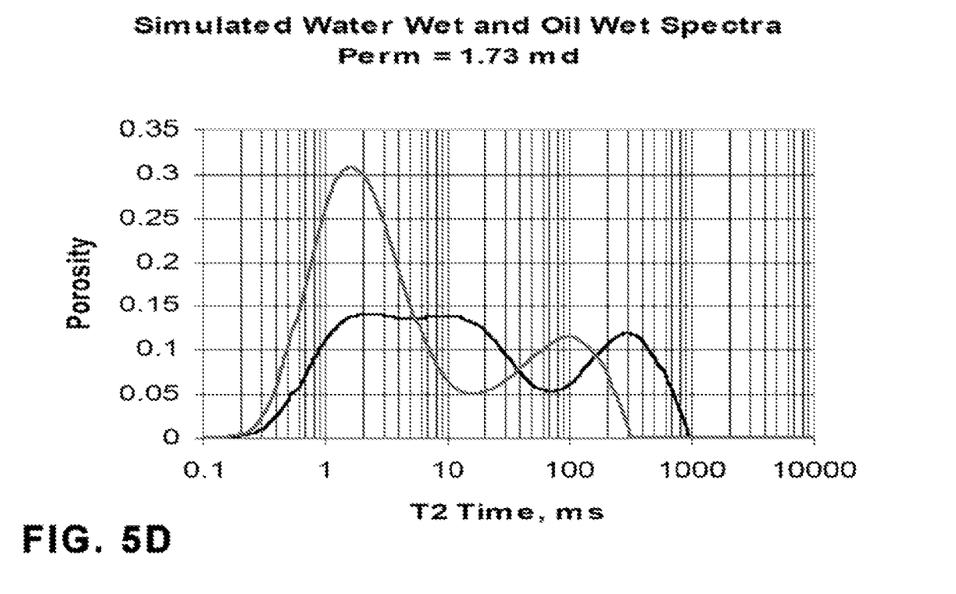
Figure 6A:
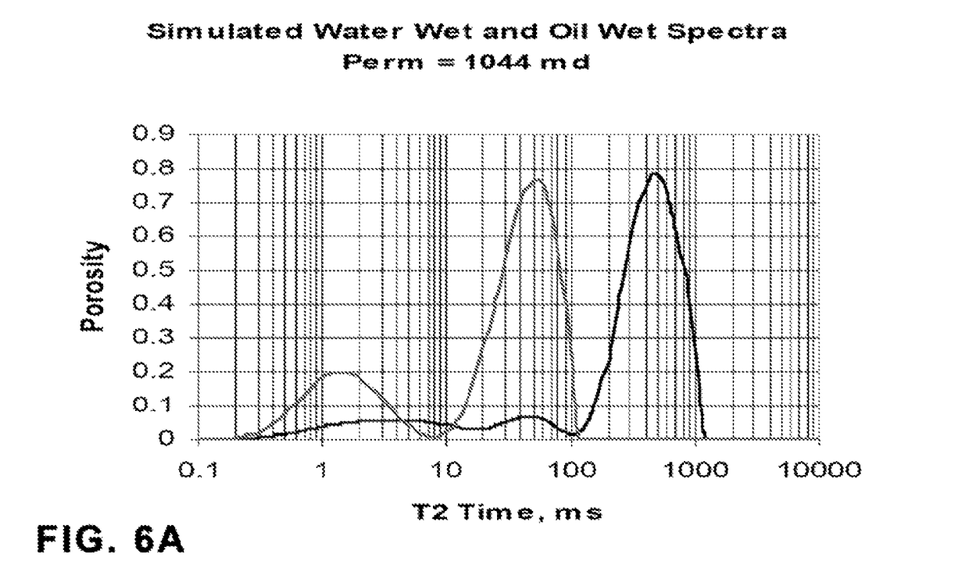
FIGS. 6a-6d show illustrative oil-wet and water-wet T2 distributions for different permeabilities for a relaxivity ratio of 3.
Figure 6B:
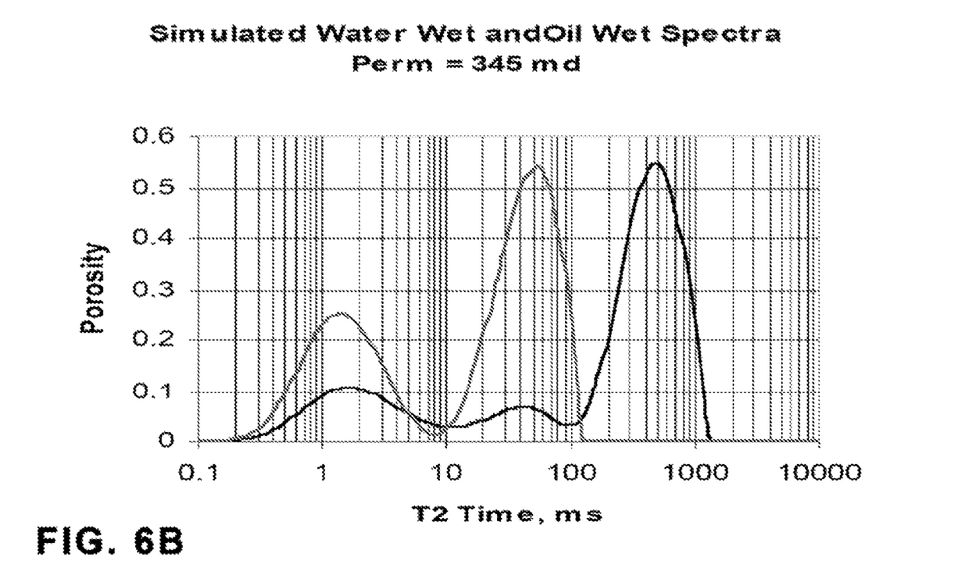
Figure 6C:
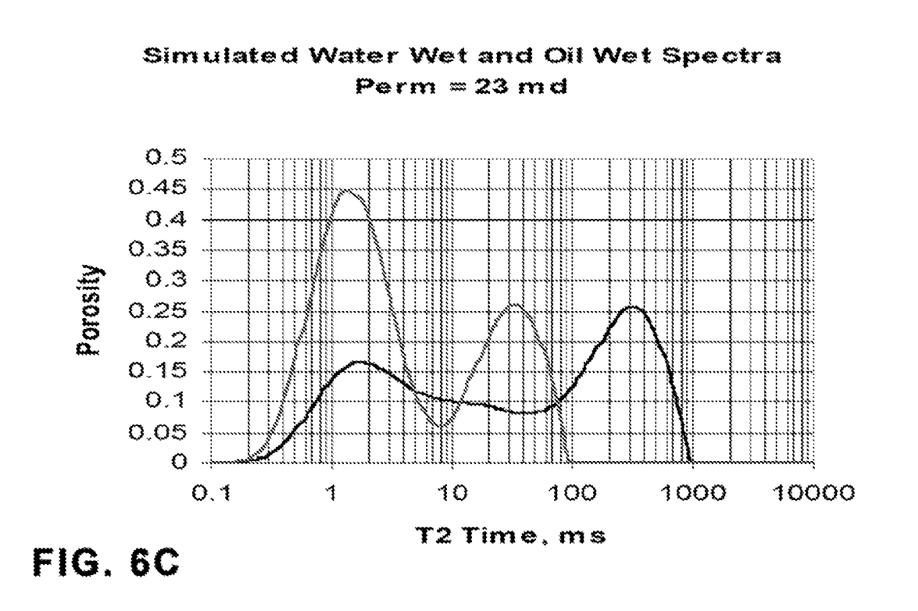
Figure 6D:
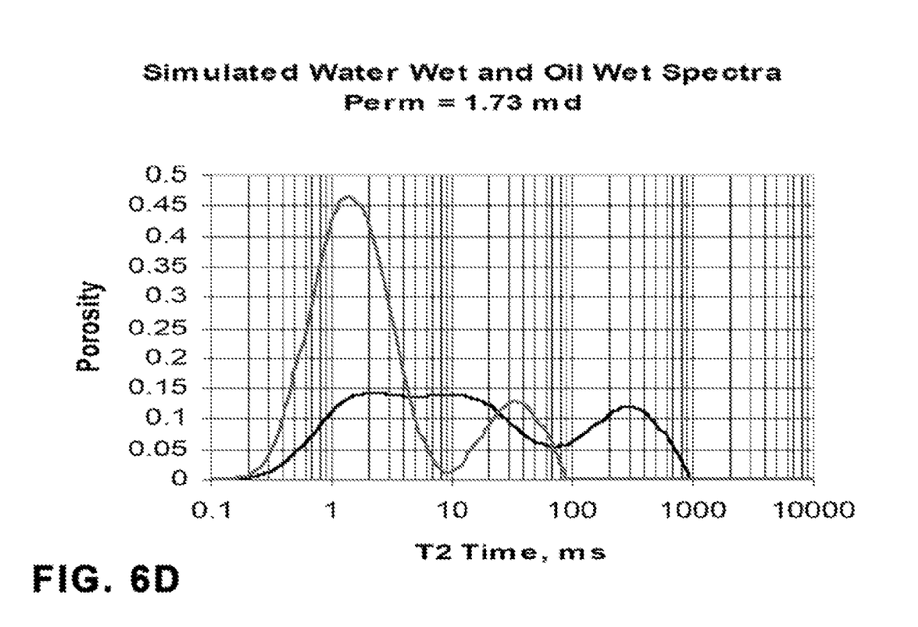

The permeability K can then be calculated:

$$\log K = a \log(S_b T_2)_{max} + b \quad (6)$$

where a and b are parameters determined in the laboratory. FIG. 4 shows an illustrative fit for equation (6), using dodecane (a light hydrocarbon) as the formation fluid. For FIG. 3, the ratio of Swanson parameters for curve 302 versus curve 304 is 3/2, indicating that the Swanson method too has a significant dependence on relaxivity.

To derive a new method having reduced sensitivity to surface relaxivity ρ, the authors begin by extrapolating from equation (2) (and the invariance of S/V for a given material) a relationship between relaxivity and relaxation time. That is:

$$\left(\frac{1}{T_{2,Oil}}\right) = \frac{\rho_O}{\rho_W}\left(\frac{1}{T_{2,Water}}\right) \quad (7)$$

This relationship enables the echo signal for oil wet formations to be predicted from the T2 distribution measured from a water wet formation:

$$(E_i)_{Oil} = \sum_{k=1}^{k=N} \phi_k e^{-\frac{\rho_O}{\rho_W}\frac{t_i}{(T_2)_k}}, \quad (8)$$

$$i = 0, 1, 2, 3, \ldots$$

This echo signal can then be inverted to obtain the T2 distribution for oil-wet formations, enabling the oil-wet and water-wet curves to be readily compared.

Figure 7:
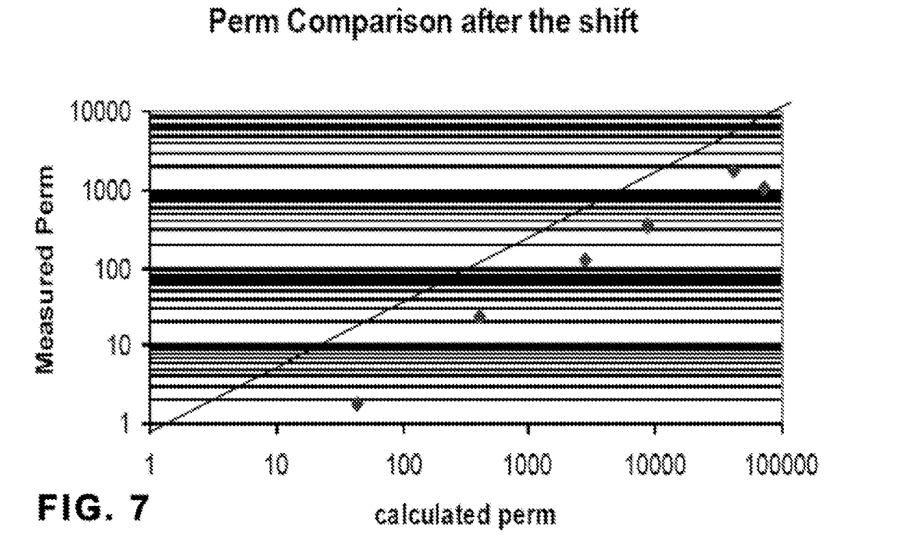
FIG. 7 shows an illustrative comparison of measured and calculated permeabilities.

FIGS. 5A-5D show the T2 distributions for water wet and oil wet formations having laboratory-measured permeabilities of 1044 mD, 345 mD, 23 mD, and 1.73 mD, respectively. The T2 distributions for the oil-wet formations are derived from the water wet distributions as outlined above, assuming a relaxivity ratio ($\rho_O/\rho_W$)=3. As can be seen, the oil-wet distributions are shifted leftward from the water-wet distributions. FIGS. 6A-6D show the same distributions with a relaxivity ratio ($\rho_O/\rho_W$)=10. The leftward shift is even more pronounced. FIG. 7 shows how the calculated permeabilities deviate from the measured permeabilities for this latter case. When the relaxivity is increased, any system relying on one of the existing permeability determination methods consistently calculates a permeability greater than the actual permeability.

Relying on the proportionality between incremental porosity $\phi_k$ and pore size $(S/V)_k$, the authors employed the foregoing equations (2) and (7) to express the Swanson parameter for a formation under the oil-wet and water-wet conditions:

$$(S_b T_2)_{max,W} \approx \max_{i \in 1 \ldots N}\left[\frac{(T_{2,W})_i}{\rho_W}\sum_{k=i}^{k=N}\frac{1}{(T_{2,W})_k}\right] \quad (9)$$

$$(S_b T_2)_{max,O} \approx \max_{j \in 1 \ldots N}\left[\frac{(T_{2,O})_j}{\rho_O}\sum_{k=j}^{k=N}\frac{1}{(T_{2,O})_j}\right] \quad (10)$$

If the bins are adjusted so that each $(T_{2,O})_k = (\rho_W/\rho_O)(T_{2,W})_k$, then it is expected that the bin indices i and j in equations (9) and (10) will be equal, and consequently $$(S_b T_2)_{max,W} = \frac{\rho_O}{\rho_W}(S_b T_2)_{max,O} \quad (11)$$

Accordingly, if the relaxivity ratio between the formation fluid and the fluid used to calibrate the Swanson method in the laboratory (usually water) is known, the Swanson method can be corrected with the scale factor ($\rho_O/\rho_W$) to remove the relaxivity dependence. If, however, this ratio is unknown, an alternative is to find this ratio from the measured T2 distribution. Specifically, if the T2 distribution is always divided in a consistent manner so that, e.g., the range between the first and last incremental porosity values above a threshold ($\phi_1$ and $\phi_N$, respectively) is always divided into N=100 bins, then equation (7) holds. We define a normalized Swanson parameter (hereafter the "Oraby parameter") as:

$$\Omega = \frac{(S_b T_2)_{max}}{\sum_{k=1}^{k=i_{max}}(T_2)_k}, \quad (12)$$

where $i_{max}$ is the bin index used to calculate the Swanson parameter. With the consistent binning assumption outlined above, the Oraby parameter provides a relaxivity-insensitive (and hence fluid-type insensitive) measure of permeability. Note that the limits on the summation in the denominator can be chosen somewhat arbitrarily, so long as they are chosen consistently. Thus, for example, the summation limits could be 1,N, or i,j where $1 \leq i \leq j \leq N$, or $1, i_{max}$, or $i_{max}, N$.

In an alternative approach, the strict binning consistency can be relaxed by using a difference in the denominator, e.g.,:

$$\Omega' = \frac{(S_b T_2)_{max}}{(T_2)_N - (T_2)_1}, \quad (13a)$$

where $(T_2)_1$ and $(T_2)_N$ are the first and last bins having incremental porosities above a threshold. It should be recognized that equation (13a) can be rewritten $$\Omega' = \max_{i \in 1 \ldots N}\left[\frac{(T_2)_i \sum_{k=i}^{k=N}\phi_k}{(T_2)_N - (T_2)_1}\right] \quad (13b)$$

so that the Oraby parameter can be found without separately determining the Swanson parameter.

In either approach the Oraby parameter is then related to permeability K as measured in the laboratory:

$$\log K = a \log \Omega + b \quad (14)$$

Figure 8:
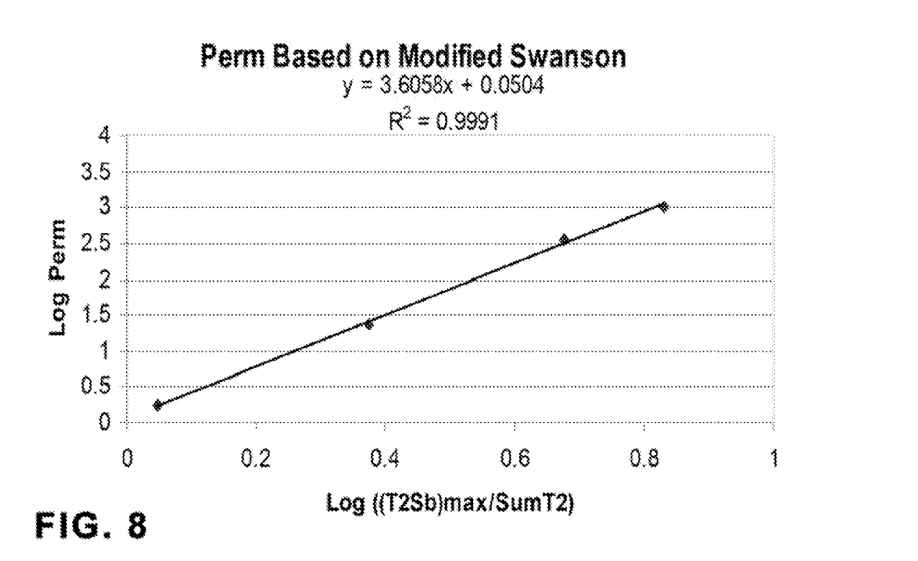
FIG. 8 shows an illustrative relationship between permeability and the Oraby parameter.

Using the examples in FIG. 6A-6D and the Oraby parameter formulation in equation (12), a=3.6058 and b=0.0504. FIG. 8 shows the quality of this linear fit.

Figure 9:
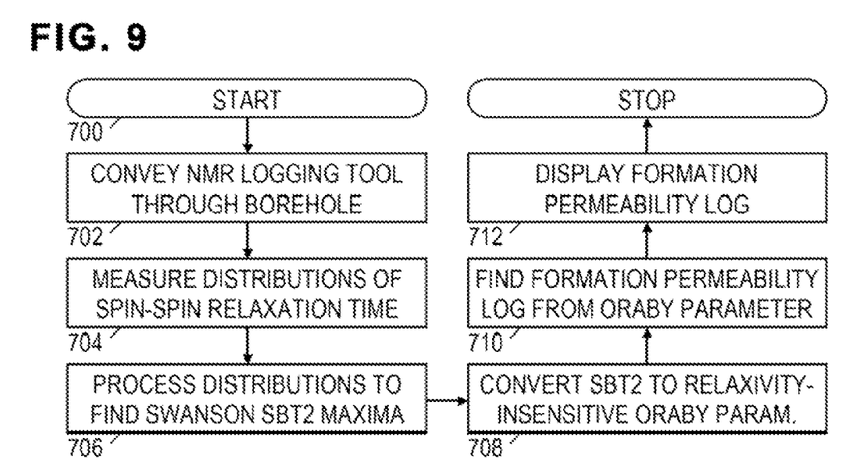
FIG. 9 shows an illustrative method for relaxivity-insensitive measurements of formation permeability.

FIG. 9 shows an illustrative method 700 for obtaining relaxivity-insensitive measurements of formation permeability. Block 702 represents the step of conveying the NMR tool through a borehole, e.g., as part of a LWD assembly or a wireline sonde. In block 704, the NMR tool employs static and radio frequency magnetic fields to orient formation nuclei and measure their relaxation responses. The tool or some other component of the system then converts the relaxation responses into measurements of T2 (spin-spin) relaxation time distributions at different positions along the borehole. In block 706, the system processes the distributions to determine the Swanson parameter of equation (5), and in block 708, the system converts the Swanson parameter to a relaxivity-insensitive Oraby parameter. (As mentioned previously, the operations of blocks 706 and 708 need not be separate operations.) In block 710, the Oraby parameter for each logged position in the borehole is converted to a permeability measurement, and in block 712 the permeability log is displayed to a user.

Figure 10:
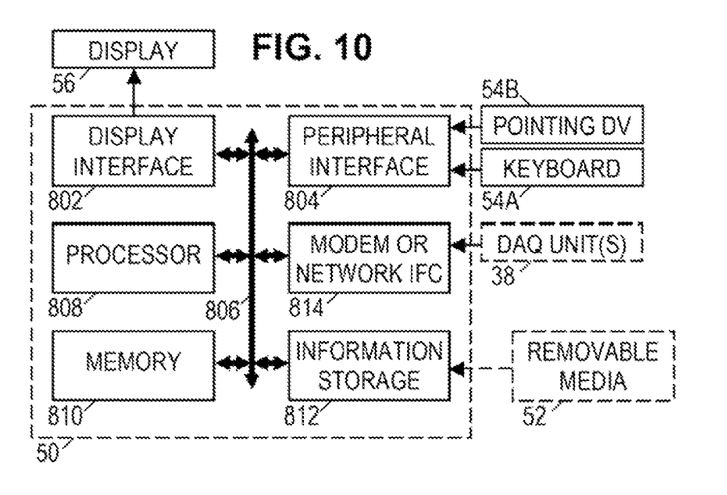
FIG. 10 shows an illustrative system for relaxivity-insensitive measurements of formation permeability.

FIG. 10 shows an illustrative system that carries out at least some of the operations in the illustrative flow diagram of FIG. 9. The system can take the form of, e.g., a desktop computer, though other data processing systems are known and can be employed. The illustrative system includes a computer chassis 50 having a display interface 802, a peripheral interface 804, a bus 806, a processor 808, a memory 810, an information storage device 812, and a network interface 814. The display interface 802 may take the form of a video card or other suitable interface that accepts information from the bus 806 and transforms it into a form suitable for display 56. Conversely, the peripheral interface may accept signals from input devices 54A, 54B and transform them into a form suitable for communication on bus 806. Bus 806 interconnects the various elements of the computer and transports their communications.

Processor 808 gathers information from the other system elements, including input data from the peripheral interface 804 and program instructions and other data from the memory 810, the information storage device 812, or from a data acquisition device 36 (FIG. 1) and other remote locations via the network interface 814. (The network interface 814 enables the processor 808 to communicate with remote systems via a wired or wireless network.) The processor 808 carries out the program instructions and processes the data accordingly. The program instructions may further configure the processor 808 to send data to other system elements, including information for the user, which may be communicated via the display interface 802 and the display 56.

The processor 808, and hence the computer as a whole, generally operates in accordance with one or more programs stored on an information storage device 812. One or more of the information storage devices may store programs and data on removable storage media such as a floppy disk or an optical disc 52. Whether or not the information storage media is removable, the processor 808 may copy portions of the programs into the memory 810 for faster access, and may switch between programs or carry out additional programs in response to user actuation of the input device. The additional programs may be retrieved from information the storage device 812 or may be retrieved from mote locations via the network interface 814. One or more of these programs configures the computer to acquire data from data acquisition unit 36 and carry out at least one of the relaxivity-insensitive permeability logging methods disclosed herein.

Figure 11:
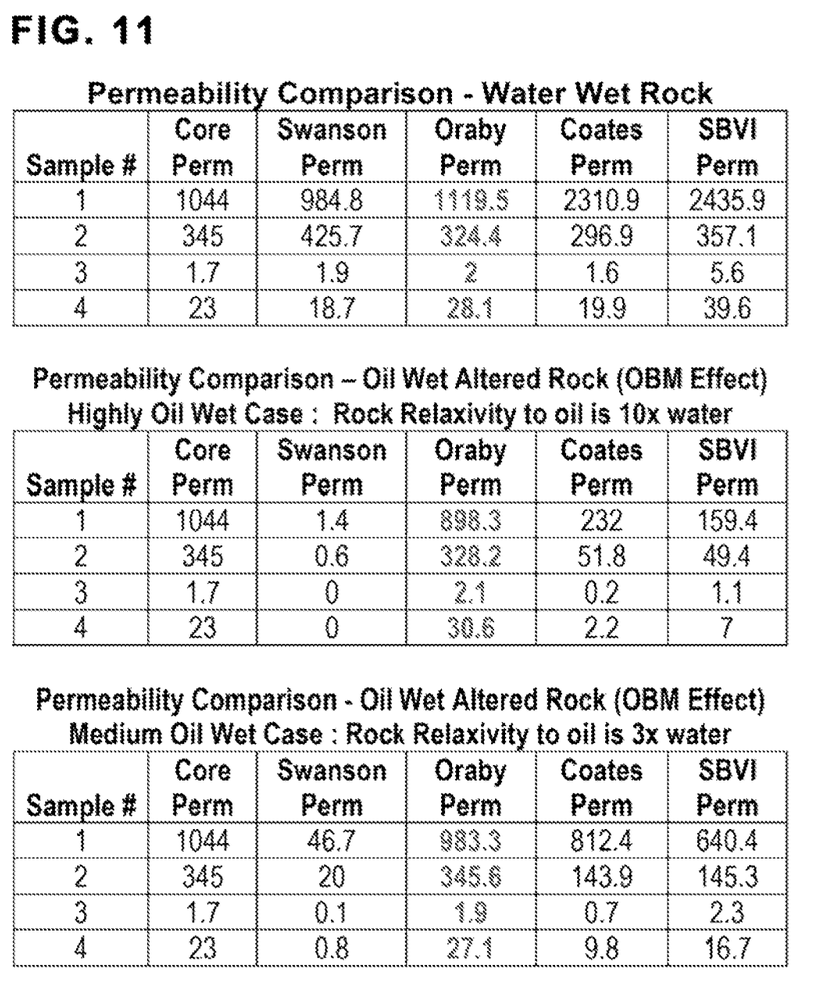
FIG. 11 provides a table comparing permeability values derived in various ways for different fluids.

FIG. 11 compares the results produced by the relaxivity-insensitive permeability measurement methods and systems disclosed herein (fourth column) with results produced by laboratory measurement of permeability (second column), Swanson method (third column), Coates method (fifth column) and the SBVI method (last column). The first table compares results for water-wet sample cores having the T2 distributions shown in both FIGS. 5 and 6. The second table compares results for oil-wet sample cores with a relaxivity ratio of 10 corresponding to the T2 distributions shown in FIGS. 6a-6d. The third table compares results for oil-wet samples cores with a relaxivity ratio of 3 corresponding to the T2 distributions shown in FIGS. 5a-5d. Clearly, the relaxivity-insensitive approach offers the most consistent— mobility measurements.

Numerous variations and modifications will become apparent to those skilled in the art once the above disclosure is fully appreciated. For example, the disclosed logging systems and methods have been described in a logging while drilling environment, but they can be readily adapted for use in a wireline or tubing-conveyed logging application. As another example, the disclosed systems and methods split the processing between downhole and surface components, but the processing can be redistributed as desired to perform a greater or lesser degree of processing uphole or downhole, even going so far as to perform all of the processing downhole if desired it is intended that the following claims be interpreted to embrace all such variations and modifications.

What is claimed is:
1. A logging system that comprises:
a logging tool assembly that provides measurements indicative of formation fluid nuclei spin-spin relaxation time distributions; and
a processor that derives, based at least in part on said measurements, a relaxivity-insensitive permeability log.
2. The logging system of claim 1, further comprising a display that shows a representation of said permeability log.
3. The logging system of claim 1, wherein said distributions are expressible as incremental porosity $\phi_i$ versus spin-spin relaxation time $(T_2)_i$, i ranging from 1 to N, where N is a number of bins in each of the distributions, and wherein as part of deriving said permeability log, the processor:
determines for each distribution a value indicative of Swanson parameter

$$(S_b T_2)_{max} = \max_{i \in 1 \ldots N} \left[ (T_2)_i \sum_{k=i}^{k=N} \phi_k \right];$$

scales said values by approximately $1/\Sigma_{k=1}^{k=i_{max}}(T_2)_k$ (where $i_{max}$ is the index that yields the Swanson parameter) to obtain respective relaxivity-insensitive parameter values; and
converts said relaxivity-insensitive parameter values into corresponding permeability values.
4. The logging system of claim 3, wherein said converting exploits a linear relationship between a logarithm of the permeability and a logarithm of the relaxivity-insensitive parameter values.
5. The logging system of claim 4, wherein said linear relationship is predetermined based on laboratory experiments with core samples.
6. The logging system of claim 1, wherein the logging tool assembly is part of a drill string.
7. The logging system of claim 1, wherein the logging tool assembly is part of a wireline sonde or tubing-conveyed sonde.
8. The logging system of claim 1, wherein the logging tool assembly includes a nuclear magnetic resonance tool that employs a Carr-Purcell-Meiboom-Gill (CPMG) pulse sequence.

9. A logging method that comprises:
   conveying a logging tool assembly along a borehole to obtain measurements indicative of formation fluid nuclei spin-spin relaxation time distributions;
   processing said measurements to generate a relaxivity-insensitive permeability log; and
   providing said permeability log to a user.

10. The logging method of claim 9, wherein said distributions are expressible as incremental porosity $\phi_i$ versus spin-spin relaxation time ($T_2$), i ranging from 1 to N, where N is a number of bins in each of the distributions, and wherein said processing includes:
   determining for each distribution a value indicative of Swanson parameter $$(S_bT_2)_{max} = \max_{i \in 1 \ldots N} \left[ (T_2)_i \sum_{k=i}^{k=N} \phi_k \right];$$

scaling said values by approximately $1/\Sigma_{k=1}^{k=i_{max}}(T_2)_k$ (where $i_{max}$ is the index that yields the Swanson parameter) to obtain respective relaxivity-insensitive parameter values; and
   converting said relaxivity-insensitive parameter values into corresponding permeability values.

11. The method of claim 10, wherein said converting exploits a linear relationship between a logarithm of the permeability and a logarithm of the relaxivity-insensitive parameter values.

12. The method of claim 11, wherein said linear relationship is predetermined based on laboratory experiments with core samples.

13. The method of claim 9, wherein said conveying is done with a tubing string or a wireline.

14. The method of claim 9, wherein said conveying is done with a drill string.

15. The method of claim 9, wherein the logging tool assembly includes a nuclear magnetic resonance tool that employs a Carr-Purcell-Meiboom-Gill (CPMG) pulse sequence.

16. An information storage medium that when placed in operable relation to a computer provides software instructions that cause the computer to:
   obtain measurements indicative of formation fluid nuclei spin-spin relaxation time distributions;
   process said measurements to generate a relaxivity-insensitive permeability log; and
   provide said permeability log to a user.

17. The information storage medium of claim 16, wherein said distributions are expressible as incremental porosity $\phi_i$ versus spin-spin relaxation time ($T_2$), i ranging from 1 to N, where N is a number of bins in each of the distributions, and wherein as part of said processing the software instructions cause the computer to:
   determine for each distribution, value indicative of Swanson parameter $$(S_bT_2)_{max} = \max_{i \in 1 \ldots N} \left[ (T_2)_i \sum_{k=i}^{k=N} \phi_k \right];$$

scale said values by approximately $1/\Sigma_{k=1}^{k=i_{max}}(T_2)_k$ (where $i_{max}$ is the index that yields the Swanson parameter) to obtain respective relaxivity-insensitive parameter values; and
   convert said relaxivity-insensitive parameter values into corresponding permeability values.

18. The information storage medium of claim 17, wherein said converting exploits a linear relationship between a logarithm of the permeability and a logarithm of the relaxivity-insensitive parameter values.

19. The information storage medium of claim 18, wherein said linear relationship is predetermined based on laboratory experiments with core samples.

\* \* \* \* \*